United States Patent [19]

Forster et al.

[11] Patent Number: 4,822,357

[45] Date of Patent: Apr. 18, 1989

[54] AUXILIARY ARTIFICIAL HEART

[75] Inventors: David A. Forster, Drayton Plains; W. Kenneth Crowder, Davison, both of Mich.

[73] Assignee: Articor Limited, Flint, Mich.

[21] Appl. No.: 43,870

[22] Filed: Apr. 29, 1987

[51] Int. Cl.$^4$ .............................................. A61F 2/22
[52] U.S. Cl. ........................................ 623/3; 600/17; 128/DIG. 3
[58] Field of Search ............ 623/3; 128/1 D, DIG. 3; 600/16, 17

[56] References Cited

U.S. PATENT DOCUMENTS

| | | | |
|---|---|---|---|
| 4,240,409 | 12/1980 | Robinson et al. | 128/1 D |
| 4,277,706 | 7/1981 | Isaacson | 128/1 D |
| 4,573,997 | 3/1986 | Wisman et al. | 623/3 |

OTHER PUBLICATIONS

"A Cam-Type Electric Motor-Driven Left Ventricular Assist Device" by G. Rosenberg et al., *Journal of Biomechanical Engineering*, vol. 104, Aug. 1982, pp. 214–220.
"Experimental Results for Chronic Left Ventricular Assist and Total Artificial Heart Development" by Y. Nose et al., *Artificial Organs*, vol. 7, No. 1, 1983, pp. 55–63.
"Design of Pusher-Plate-Type Left Ventricular Assist Device Based on Mechanical Analyses" by K. Hayashi et al., *Artificial Organs*, vol. 8, No. 2, 1984, pp. 204–214.
"Investigations with an Implantable, Electrically Actuated Ventricular Assist Device" by W. Bernard et al, *J. Thorac Cardiovasc Surg.* vol. 88, No. 1, Jul. 1984, pp. 11–21.

*Primary Examiner*—Ronald L. Frinks
*Attorney, Agent, or Firm*—Barnes, Kisselle, Raisch, Choate, Whittemore & Hulbert

[57] ABSTRACT

An auxiliary artificial heart which comprises a pump having a single opening that is connected to the aorta and is operable in synchronism with the heart of the patient to assist the normal function of the heart. The auxiliary artificial heart comprises a housing having the single opening therein and a diaphragm which is movable toward and away from the opening by a rotating reversible electric stepping motor. Rotation of the motor rotates circumferentially spaced roller pins which extend radially inwardly into engagement with a helical groove of a screw attached to the diaphragm such to translate the screw and move the diaphragm toward and away from the opening. The housing is sealed to enclose a gas in the housing such that the differential pressure caused by movement of the screw assists the diaphragm in its movement.

12 Claims, 5 Drawing Sheets

WITH PUMP

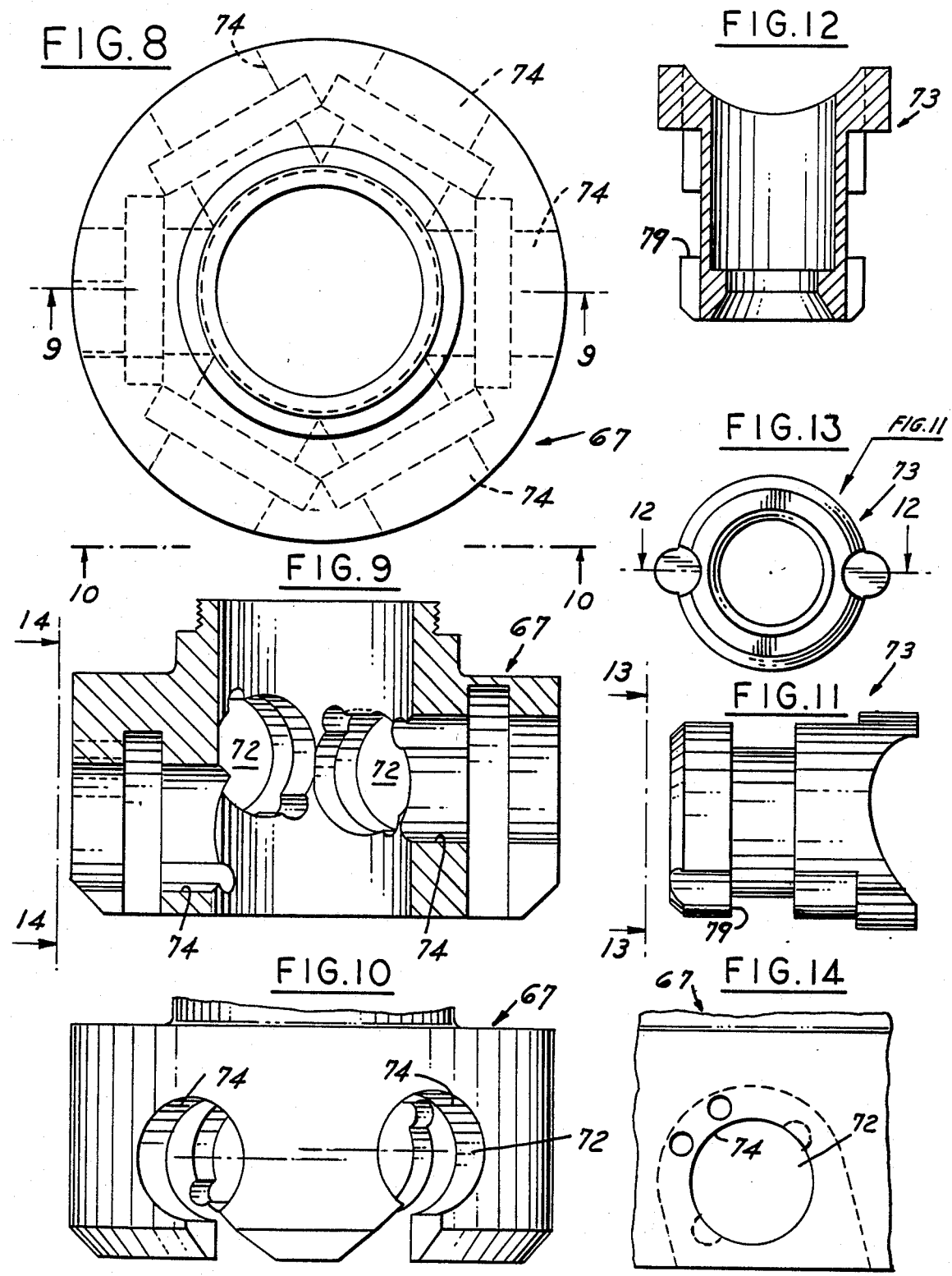

AUXILIARY ARTIFICIAL HEART

This invention relates to auxiliary artificial hearts.

BACKGROUND AND SUMMARY OF THE INVENTION

It has been known that heart patients may benefit from total artificial hearts. Such patients include those who die from pump failure following open heart surgery, patients who have intractable heart failure and patients who die from cardiogenic shock. A greater number could be saved by providing an auxiliary heart or pump in the cardiovascular system. It is heretofore been proposed that a left ventricular assist pump be provided in a line between the left ventricle and the aorta which functions to bypass some of the blood and thereby assist the heart.

The advantage of a left ventricular assist device is that it assists the human heart in maintaining its pump action, alters the physiology of the patient to a lesser degree and is less likely to interfere with other body functions. Theoretically, the device would require less energy allowing the energy source to be smaller.

Left ventricular assist devices which are provided between the left ventricle and the aorta function to draw blood from the left ventricle and bypass the blood through a pump to the aorta. Among the types that have been proposed are "A CamType Electric Motor-Driven Left Ventricular Assist Device", Rosenberg et al, *Journal of Biomechanical Engineering*, Vol. 104, 1982, p. 214–220; "Experimental Results for Chronic Left Ventricular Assist and Total Artificial Heart Developement", Y. Nose et al, *ARTIFICIAL ORGANS*, Vol. 7, No. 1, 1983, p. 55–63; "Design of Pusher-Plate-Type Left Ventricular Assist Device Based on Mechanical Analyses", K. Hayashi et al, *ARTIFICIAL ORGANS*, Vol. 8, No. 2, 1984, p. 204–214; "Investigations With an Implantable, Electrically Actuated Ventricular Assist Device", Bernard, et al J. Thorac Cardiovasc Surg 88; 11–21, 1984.

Among the objectives of the present invention are to provide an auxiliary artificial heart which is easier to attach because it is adapted to be connected to the aorta only; which is compact, durable, efficient, light weight, has a low inertia; which can be adjusted to provide or change volume and wherein the diaphragm may be readily renewed or replaced.

In accordance with the invention the auxiliary artificial heart comprises a pump having a single opening that is connected to the aorta and is operable in synchronism with the heart of the patient to assist the normal function of the heart. The auxiliary artificial heart comprises a housing having the single opening therein and a diaphragm which is movable toward and away from the opening by a rotating reversible electric stepping motor. Rotation of the motor rotates circumferentially spaced roller pins which extend radially inwardly into engagement with a helical groove of a screw attached to the diaphragm to translate the screw and move the diaphragm toward and away from the opening. The housing is sealed such that the differential pressure caused by movement of the screw assists the diaphragm in its movement.

DESCRIPTION OF THE DRAWINGS

FIG. 8 is a plan view of another portion of the artificial heart.

FIG. 9 is a sectional view taken along the line 9—9 in FIG. 8.

FIG. 10 is a fragmentary view taken along the line 10—10 in FIG. 8.

FIG. 11 is a side elevational view of another part utilized in the artificial heart.

FIG. 12 is a sectional view taken along the line 12—12 in FIG. 13.

FIG. 13 is a view taken along the line 13—13 in FIG. 11.

FIG. 14 is a fragmentary view taken along the line 14-14 in FIG. 9.

DESCRIPTION

Figure 1:
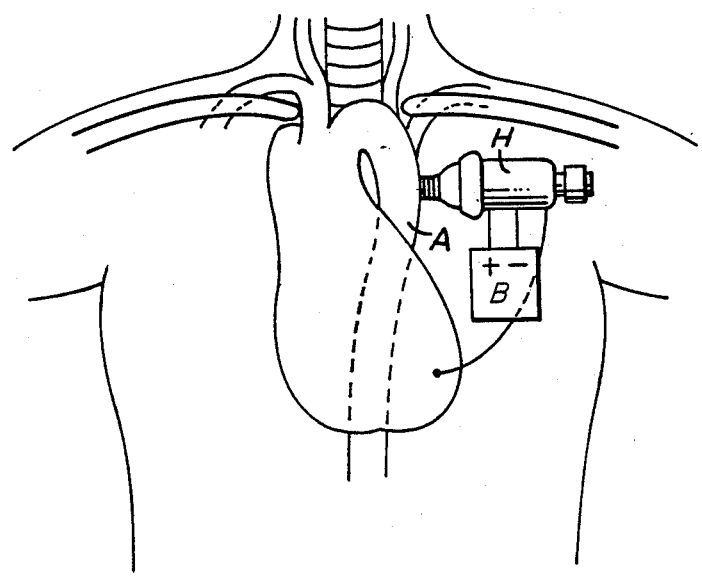
FIG. 1 is a schematic of a cardiovascular system showing the manner in which the auxiliary artificial heart embodying the invention is connected to the system.
Figure 2:
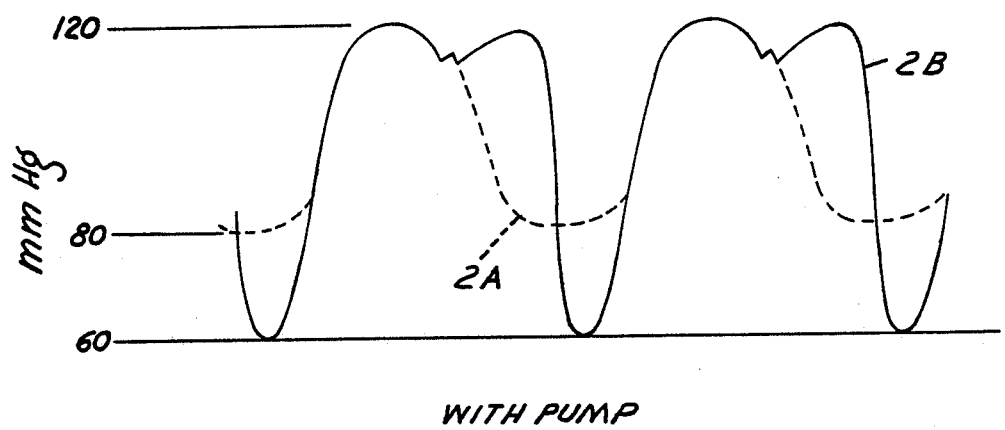
FIG. 2 comprises curves of heart pressure versus pump

In accordance with the invention as shown in FIG. 1, the auxiliary artificial heart H is connected directly through a single opening to the aorta A. It is attached to the aorta in the chest cavity, just distal to the left subclavian artery. Thus if emboli do occur, there will be less chance of the passage to the brain and producing a stroke. The device will be attached to the chest wall in a suitable manner. Part of one or two ribs and some muscle of the chest wall will be removed to form a suitable pocket. This pocket will reduce the compressive interference of lung expansion. The device works in synchronization with the heart. The chamber of the pump fills in late diastoli, reducing the patient's diastolic pressure. This reduced diastolic pressure reduces the afterload of the heart, allowing the heart to eject its blood volume with less work expenditure. After the heart has ejected its volume during systoli, the aortic valve is closed. The pump device then ejects its volume in early diastolic to enhance the circulatory flow of blood to the body and to the coronary arteries providing more oxygen to the tissues. Referring to FIG. 2, curve 2A is the normal pressure curve. Curve 2B demonstrates the pressure curve noted in the aorta as the pump functions.

Figure 3:
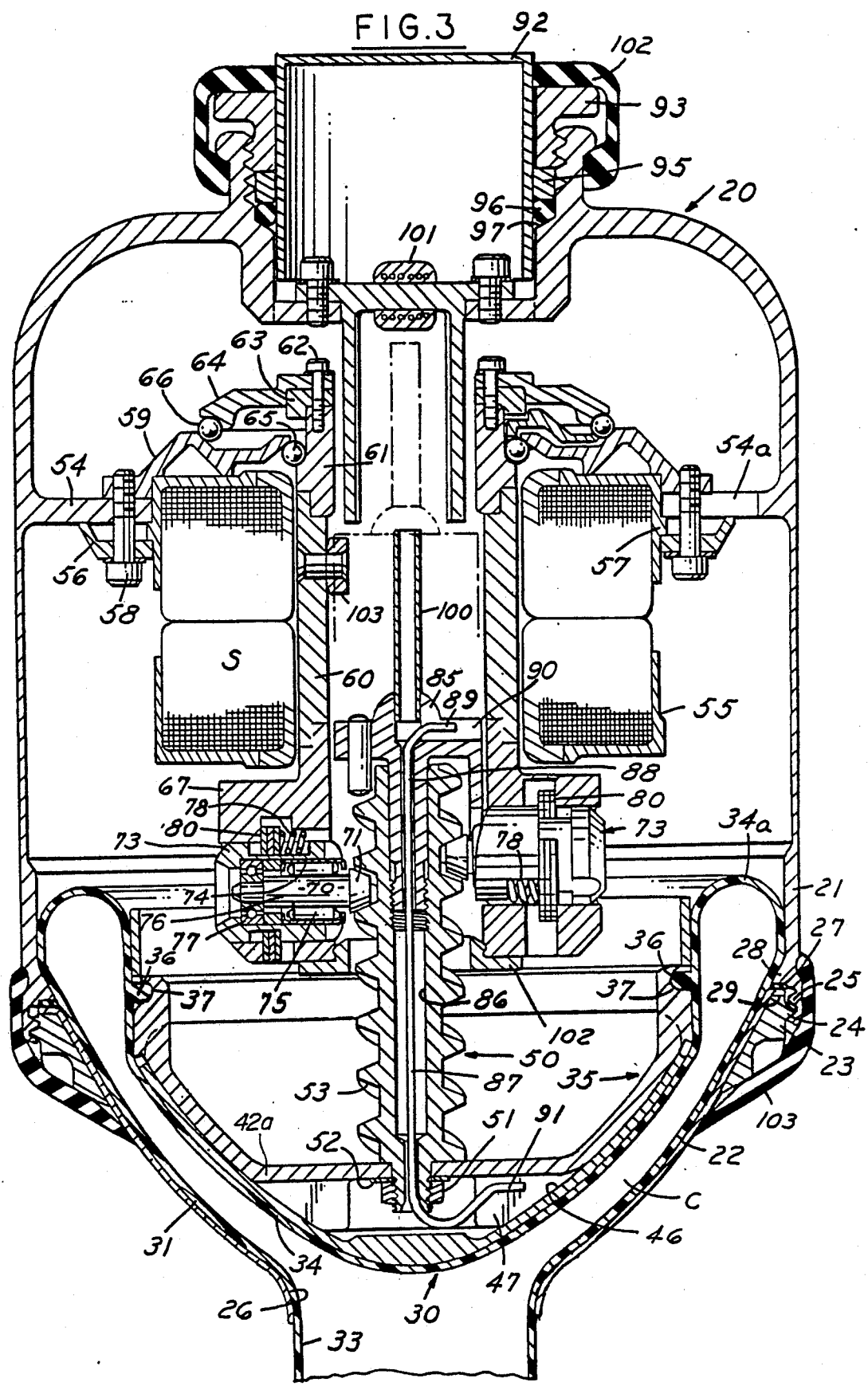
FIG. 3 is a longitudinal sectional view of the auxiliary artificial heart.

Referring to FIG. 3, the auxiliary artificial heart embodying the invention comprises a main body or housing 20 which is cylindrical in cross section and is made of a light weight material such as titanium. Housing 20 has an open end 21 on which an end cap 22 is supported by a end cap nut 23 that has an external thread 24 engaging an internal thread 25 on open end 21 of the body 20. End cap 22 has a central opening 26. A resilient seal 27 is interposed between a radially inwardly extending flange 28 on the housing 20 and a flange 29 on the periphery of the end cap 22.

A resilient diaphragm 30 is positioned within the body and includes an outer wall 31 engaging the end cap 22 and having a central tubular opening 33 that extends through the opening 26 of the end cap 22 for attachment to the aorta as by suturing. The diaphragm 30 further includes an inner wall 34 that is connected to the outer wall 31 by a connecting portion 34a and is spaced from and cooperates with the outer wall 31 to form a chamber C which changes in size depending upon the position of the inner wall 34.

Figure 4:
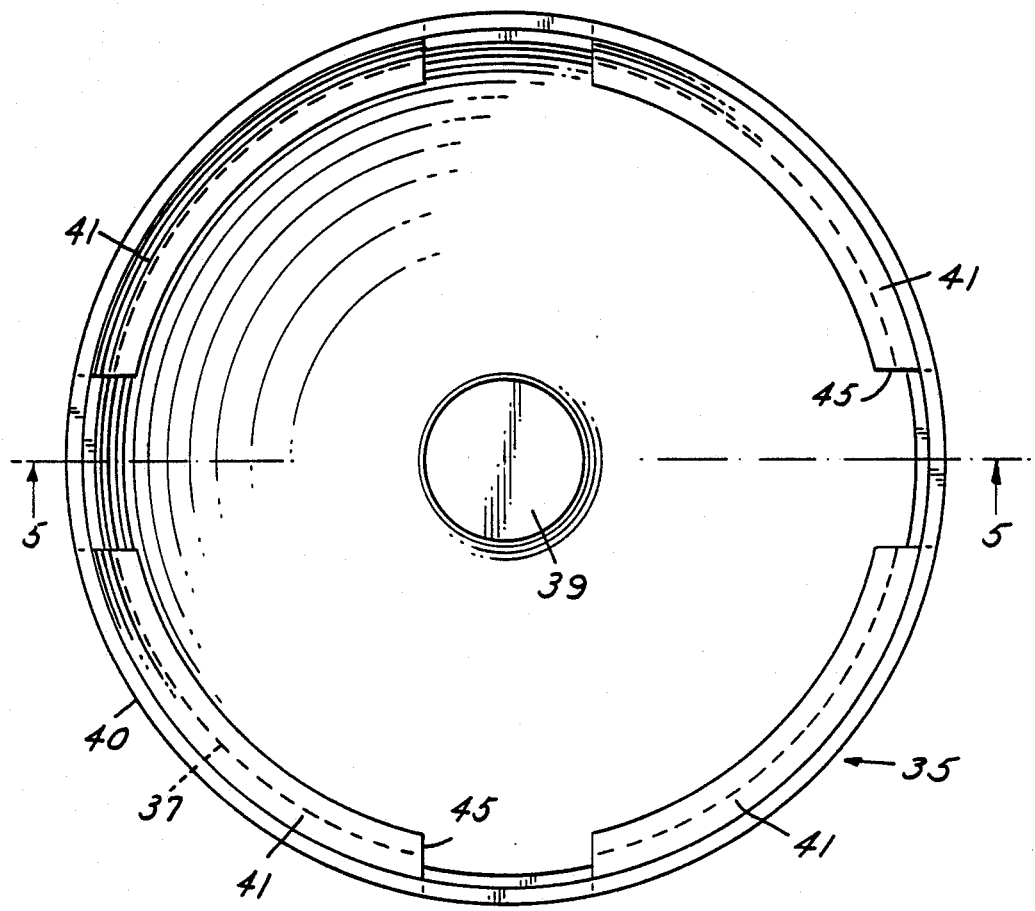
FIG. 4 is a plan view of a part of the auxiliary artificial heart.
Figure 5:
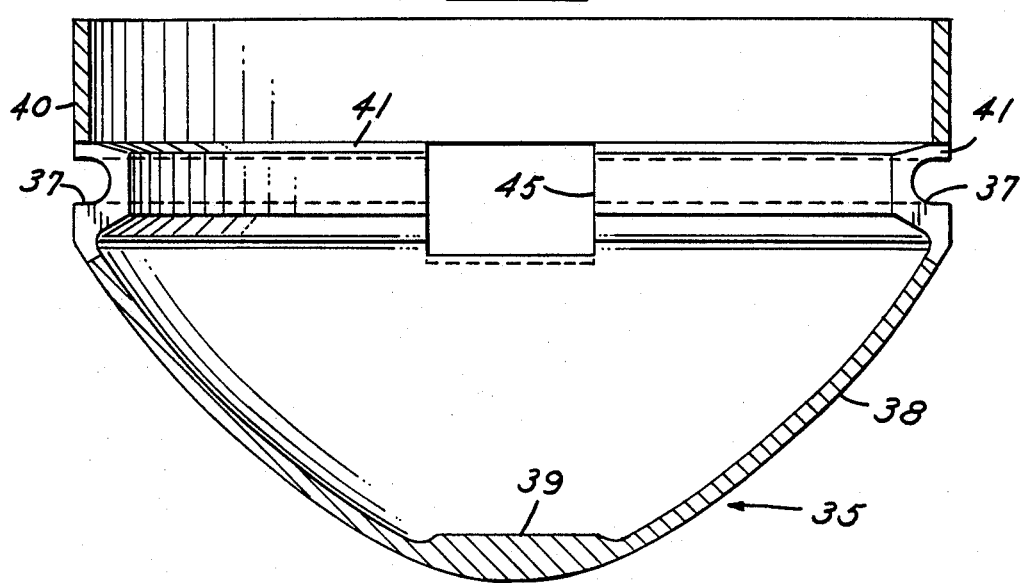
FIG. 5 is a sectional view taken along the line 5—5 in FIG. 4.

The diaphragm 30 is moved inwardly and outwardly by a piston 35 which is adhered to the wall 34. The diaphragm 30 includes an integral retaining ring 36 that engages an annular groove 37 in the piston 35 (FIG. 5). As shown in FIGS. 4 and 5, the piston 35 includes a convex external surface 38, a thickened central portion 39 and a cylindrical external surface 40 at its upper end. As shown in FIG. 4, the groove 37 is formed in flanges 41 which are circumferentially spaced so that the groove is discontinuous.

Figure 6:
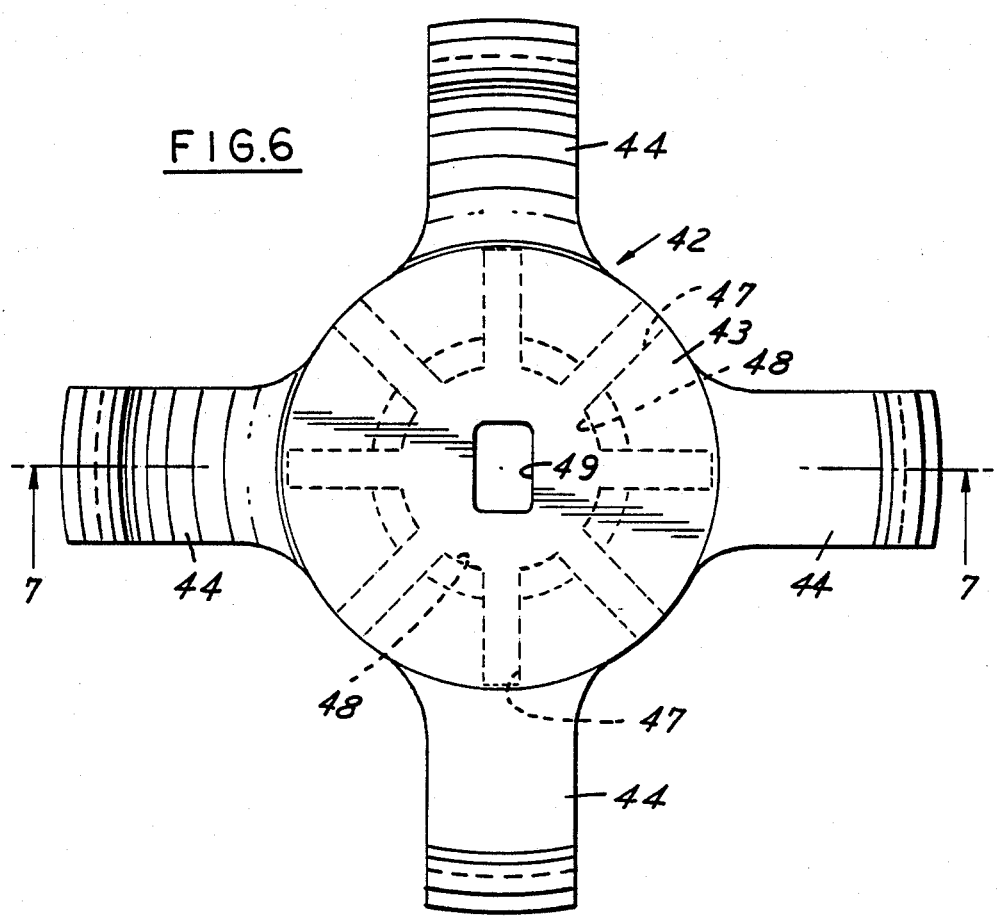
FIG. 6 is a plan view of another part of the artificial
Figure 7:
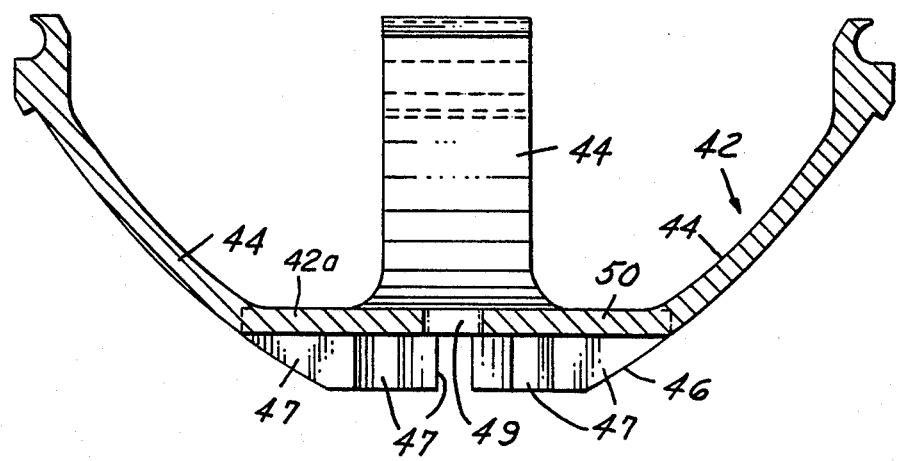
FIG. 7 is a sectional view taken along the line 7—7 in FIG. 6.

Referring to FIGS. 6 and 7, a piston adapter 42 fits within the piston 35 and comprises a central portion 43, and radial arms 44 that extend upwardly into the space 45 between flanges 41 on piston 35 to cooperate with flanges 41 and thereby define a continuous groove 37 for holding the ring 36 of the diaphragm in position. The lower end of the piston adapter 42 engages the inner surface of the piston 35 in an annular area 46 and is provided with a plurality of radially extending grooves 47 in the bottom wall 42a emanating from a central circular space 48 and a rectangular opening 49 which is centrally located along lower wall 42a. A screw 50 has its lower end shaped in a rectangular cross section and extends through the opening 49 and is held in position by a nut 51 threaded on the lower end thereof against a lock washer 52. In this fashion the screw 50 is rigidly fastened and supported on the wall 42a of the piston adapter 42.

The screw 50 is provided with a helical external thread 53 that is preferably an Acme thread.

Reciprocation of the screw 50 causes the diaphragm 30 to move upwardly and downwardly as viewed in FIG. 3 drawing blood into the chamber C defined by the diaphragm and forcing the blood outwardly.

The housing 20 includes a transverse inwardly extending flange 54 toward the upper end thereof that supports a bracket 55 which is turn supports the stator S of the electric motor. More specifically a bracket 56 engages an outwardly extending flange 57 on the bracket 55 and bolts 58 extend through slots 54a in the flange 54 into threaded engagement with an annular bearing race 59 that engages the upper end of the stator bracket 55. The armature or rotor 60 associated with the motor is supported for rotation by ball bearings. More specifically an upper extension inner race 61 is fixed to the upper end of the armature 60 which in turn supports, by a bolt 62 and a spacer 63 an outer race 64. Balls 65 are interposed between the inner race 61 and the main bearing race 59 and balls 66 are interposed between the outer race 64 and the main bearing race 59.

A lower extension 67 is provided on the armature 60 and defines a wheel that supports a plurality of radially extending roller pins 70, the inner end 71 of which are frustoconical and engage the thread 53 of the screw 50. The inner end 71 of each pin 70 is constructed and arranged to have substantially frictionless contact with the thread 53 of the screw 50. This is achieved as shown in FIG. 3 by having the axes of the frustoconical surfaces of the end 71 constructed and arranged such that the axes lines coincide with the axes of the conjugating surfaces of the thread 53.

Referring to FIGS. 8-14, each pin 70 is supported in the wheel 67 by a pin bearing housing 73 that is generally cylindrical and extends into an opening 74. Six openings 74 are provided, three at one level for engaging one side of the thread 53 and three at a different level or longitudinal position relative to the screw 50 for engaging the other side of the thread 53. Each pin 70 is mounted for rotation by roller bearings 75 which engage an intermediate cylindrical surface 76 and ball bearings 77 that engage the outer end of pin 70. At least some of the pins 70 are yieldingly urged radially inwardly by springs 78 interposed between a flange 79 and spacers 80.

A rotary stop member 85 is provided on the upper end of the screw 50 and includes a portion extending axially through a central opening 86 and threaded into the screw 50 for relative rotational adjustment of the stop 85. A torsion spring 87 extends through opening 86 in the screw 50 and an opening 88 in the stop and has an upper end 89 extending radially into a radial slot 90 in the upper end of stop 85 and a lower end 91 extending radially into one of the radial slots 47 in piston adaptor 42. The spring 87 functions as a positive stop in movement of the diaphragm 30 and screw 50 up and down, as presently described.

Referring to FIG. 3, a cop 92 is provided to close the open upper end of the housing 20. The cap 92 is held in position by a nut 93 that has an eternal thread engaging an internal thread on the housing 20 and forcing a sealing collar 95 into engagement with an O-ring 96 against an inclined surface 97 on the housing. By this arrangement the area within the housing is above the diaphragm is sealed from the exterior. A pin 100 is provided on the upper end of the screw and is associated with a coil 101 to define a variable transformer producing an electrical signal corresponding to the position of the diaphragm 30.

Upper and lower boots 102, 103 are provided for the upper and lower ends of the housing.

In accordance with the above arrangement, there is provided a screw 50 that is supported by plunger but is only guided vertically and horizontally by the pins 70 so that the only friction encountered is that between the ends 71 of the pins 70 and the thread 53. The screw 50 is thus held concentric and coaxial at all times with respect to the motor armature or stator.

Energization of the stepping motor by a proper control device such as a microcomputer positioned adjacent the patient, moves the diaphragm to pump blood as desired. The electrical signals to the stepping motor can be controlled such that they are provided as needed and such programming can be controlled so that the stroke will cease at the desired time.

The torsion spring 87 functions on a down stroke to engage a stop collar 102 and on the up stroke to engage a stop collar 85 in the event of excess movement. By this arrngement, a safety is provided but in normal operation the programming of the electric motor will result in no need for a stopping force by the torsion spring.

The variable transformer is preferably used as an input to the microcomputer to de-energize the motor in time to allow the motor to coast to a stop.

By sealing the space above the diaphragm 30 in the housing, a change in air pressure is achieved as the diaphragm is moved inwardly and outwardly an pressure sensors can be utilized to further control the extent of movement of the diaphragm.

The sealed chamber thus provided also serves a vital function of saving energy since the diaphragm works directly against gas or air in the chamber, the energy of the air as it is compressed is then utilized to return the diaphragm to its downward position. The provision of a non-expandable sealed chamber allows the stored energy to function at the end of each stroke recovering the energy and requiring less power for operation of the electric motor. This makes the device more efficient and serves to provide for longer life if the device is actuated by batteries.

It can thus be seen that the chamber of the device has one port. No valve is necessary to pump works in synchronization with the heart and aortic valve. The chamber defined by the diaphragm is lined with an non-thrombogenic material. This may comprise a polyurethane material with a coating of a non-reactive material such as a treated gelatin. The entire chamber is lined so that no interface is present. This should reduce buildup of pseudointima and occlusion of the orifice. This will also decrease thrombus formation and subsequent emboli. The pusher plate is projected and withdrawn to fill and empty the chamber. The pusher plate is actuated by the motor. The motor is controlled by the control module. A pressure transducer to the aorta and an EKG electrode on the heart will provide the sensing device to regulate the timing of the motor. The motor will have a battery powered source B implanted subcutaneously. This will allow recharging of the batteries through the intact skin. A nickel-cadmium battery is proposed, but a nuclear battery could also be applied if available. The control module will provide for several programmable functions. These include:

1. Adjustable timing sequence for the ejection and filling of the pump in relation to the EKG and pressure curve.
2. Change of volume, for example, from 30 ml to 100 ml as the patient requires.
3. Reducing the ejection to every other beat or every third beat as the body allows. This will decrease the energy used at night while the patient is asleep, and in some patients, during the day.
4. The pump will provide a constant rate of ejection, for example, at 50 beats per minute if it does not sense the heart beat for a time such as 20 seconds. This would provide, for example, approximately 3 L/min. of blood flow to sustain a patient who has sustained a sudden ventricular fibrillation until he can be transferred to a hospital.

These programmable functions can be regulated to the module through the intact skin as pacemaker programming is performed today.

We claim:

1. An auxiliary artificial heart comprising a housing having an opening adapted to be connected to a blood vessel,
    a diaphragm mounted in said housing for movement toward and away from the opening,
    an electric motor mounted within said housing;
    said motor including a stator and an armature, said armature being hollow,
    a screw connected to one side of said diaphragm and having an external thread thereon,
    said armature supporting a plurality of circumferentially spaced roller pins extending radially inwardly with, the ends having surfaces complementary to the surface of the thread on the screw,
    each said roller pin being supported by bearings in said armature such that when the motor is energized to rotate the armature in one direction, the screw and, in turn, the diaphragm are moved toward the opening in the housing and when the motor is energized to rotate the armature in the opposite direction, the screw is moved and, in turn, the diaphragm are moved away from the opening.

2. The auxiliary artificial heart set forth in claim 1 wherein the screw has an Acme type thread, the end of each said roller pin having a complementary frustoconical surface.

3. The auxiliary artificial heart set forth in claim 2 wherein said roller pins constitute the sole support for the screw within the housing.

4. The auxiliary artificial heart set forth in claim 3 wherein at least some of said roller pins are in engagement with one side surface of the thread and at least others of said roller pins are in engagement of another side of the thread.

5. The auxiliary artificial heart set forth in claim 4 wherein the converging point of the axes of said frustoconical surfaces and the axes of the conjugating thread surfaces is beyond the center line of the screw.

6. The auxiliary artificial heart set forth in claim 5 including means yieldingly urging each said roller pin radially inwardly toward said armature.

7. The auxiliary artificial heart set forth in claim 5 including means yieldingly urging at least some of said roller pins radially inwardly toward said armature.

8. The auxiliary artificial heart set forth in any of claims 1-5 and 7 wherein said housing includes means for sealing the side of the diaphragm opposite said opening such that the air or compressible gas on said opposite side is compressed and decompressed by the movement of the diaphragm permitting the energy of compression and decompression to be utilized in assisting the movement of the screw and diaphragm.

9. The auxiliary artificial heart set forth in claim 1 including torsion spring means functioning to limit the movement at each end of the stroke of the screw.

10. The auxiliary artificial heart set forth in claim 9 wherein said torsion spring means comprises a torsion spring member extending through an axial opening in said screw and having laterally extending end portions adapted to engage portions of the armature and the housing to limit the movement of the screw relative to the armature.

11. The auxiliary artificial heart set forth in claim 1 including means for retaining said diaphragm comprising a piston which is attached to the screw and means removably connecting the diaphragm to the piston.

12. The method of providing auxiliary blood to a patient which comprises
    positioning a pump within the chest cavity which pump has a single opening and means for reciprocating a piston toward and away from the opening, and
    connecting the opening to the aorta at a point distal to the left subclavian artery.

* * * * *